United States Patent
Burmeister et al.

(10) Patent No.: US 6,451,052 B1
(45) Date of Patent: Sep. 17, 2002

(54) TISSUE SUPPORTING DEVICES

(75) Inventors: Paul H. Burmeister, Maple Grove, MN (US); Charles L. Euteneuer, St. Michael, MN (US); Brian J. Brown, Hanover, MN (US); Paul J. Fordenbacher, Minneapolis, MN (US); Anthony C. Vrba, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/172,590

(22) Filed: Oct. 14, 1998

Related U.S. Application Data

(60) Division of application No. 08/737,492, filed as application No. PCT/US95/06228 on Mar. 18, 1995, and a continuation-in-part of application No. 08/246,320, filed on May 19, 1994, now abandoned.

(51) Int. Cl.[7] .................................................. A61F 2/06
(52) U.S. Cl. ..................... 623/1.16; 623/1.19; 623/1.44
(58) Field of Search .............................. 623/1.16, 1.17, 623/1.18, 1.19, 1.2, 1, 44, 23.7; 606/195, 198

(56) References Cited

U.S. PATENT DOCUMENTS

| | | |
|---|---|---|
| 3,012,883 A | 12/1961 | Muldawer et al. |
| 3,174,851 A | 3/1965 | Buehler et al. |
| 3,585,647 A | 6/1971 | Gajewski et al. |
| 3,657,744 A | 4/1972 | Ersek |
| 3,808,113 A | 4/1974 | Okamura et al. |
| 3,868,956 A | 3/1975 | Alfidi et al. |
| 3,923,065 A | 12/1975 | Nozick et al. |
| 4,030,503 A | 6/1977 | Clark, III |
| 4,046,150 A | 9/1977 | Schwartz et al. |
| 4,140,126 A | 2/1979 | Choudhury |

(List continued on next page.)

FOREIGN PATENT DOCUMENTS

| | | |
|---|---|---|
| EP | 0 119 688 A2 | 9/1984 |
| EP | 0 183 372 | 6/1986 |
| EP | 0 376 132 A1 | 7/1990 |
| EP | 0 461 791 A1 | 12/1991 |
| EP | 0 508 473 A2 | 10/1992 |
| EP | 0 546 712 A2 | 6/1993 |
| EP | 0 554 082 A1 | 8/1993 |
| EP | 0 556 850 A1 | 8/1993 |
| EP | 0 565 251 A1 | 10/1993 |
| EP | 0 380 666 B1 | 12/1993 |

(List continued on next page.)

OTHER PUBLICATIONS

"Super Elastic Nickel–Titanium Wires" by Dieter Stoeckel and Weikang Yu of Ray Chem Corporation, Menlo Park, California, Copy received Nov. 12, 1992.

Metals Handbook, Tenth Edition, vol. 2, Properties and selection: Nonferrous Alloys and Special–Purpose Materials, "Shape Memory Alloys" by Hodgson Wu and Biermann, pp. 897–902.

In Press, Titanium Handbook, ASM (1994), Section entitled Structure and Properties of Ti–Ni Alloys, by T.E. Duerig and A.R. Peltar.

Scientific American, Nov. 1979, vol. 241, No. 5, pp. 74–82, Shape–Memory Alloys.

Primary Examiner—Paul B. Prebilic
(74) Attorney, Agent, or Firm—Vidas, Arrett & Steinkraus

(57) ABSTRACT

A new multiple component stent arrangement which allows for initial self-expansion and subsequent deformation to a final enlarged size. These tissue supporting devices are generally cylindrical or tubular. They have at least one component which is deformable, by an external force, to maintain further expansion.

16 Claims, 13 Drawing Sheets

U.S. PATENT DOCUMENTS

| | | |
|---|---|---|
| 4,149,911 A | 4/1979 | Clabburn |
| 4,170,990 A | 10/1979 | Baumgart et al. |
| 4,244,140 A | 1/1981 | Kim |
| 4,300,144 A | 11/1981 | Bokros |
| 4,306,318 A | 12/1981 | Mano et al. |
| 4,313,231 A | 2/1982 | Koyamada |
| 4,319,363 A | 3/1982 | Ketharanathan |
| 4,326,532 A | 4/1982 | Hammar |
| 4,347,846 A | 9/1982 | Dormia |
| 4,425,908 A | 1/1984 | Simon |
| 4,435,853 A | 3/1984 | Blom et al. |
| 4,466,139 A | 8/1984 | Ketharanathan |
| 4,503,569 A | 3/1985 | Dotter |
| 4,509,517 A | 4/1985 | Zibelin |
| 4,512,338 A | 4/1985 | Balko et al. |
| 4,547,156 A | 10/1985 | Hader |
| 4,553,545 A | 11/1985 | Maass et al. |
| 4,560,374 A | 12/1985 | Hammerslag |
| 4,572,186 A | 2/1986 | Gould et al. |
| 4,577,631 A | 3/1986 | Kreamer |
| 4,580,568 A | 4/1986 | Gianturco |
| 4,614,516 A | 9/1986 | Blom et al. |
| 4,649,922 A | 3/1987 | Wiktor |
| 4,655,771 A | 4/1987 | Wallsten |
| 4,665,906 A | 5/1987 | Jervis |
| 4,665,918 A | 5/1987 | Garza et al. |
| 4,681,110 A | 7/1987 | Wiktor |
| 4,728,322 A | 3/1988 | Wallner et al. |
| 4,729,766 A | 3/1988 | Bergentz et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,762,128 A | 8/1988 | Rosenbluth |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,817,600 A | 4/1989 | Herms et al. |
| 4,820,298 A | 4/1989 | Leveen et al. |
| 4,822,361 A | 4/1989 | Okita et al. |
| 4,830,003 A | 5/1989 | Wolff et al. |
| 4,831,094 A | 5/1989 | Stein et al. |
| 4,832,055 A | 5/1989 | Palestrant |
| 4,848,343 A | 7/1989 | Wallsten et al. |
| 4,856,516 A | 8/1989 | Hillstead |
| 4,878,906 A | 11/1989 | Lindemann et al. |
| 4,886,062 A | 12/1989 | Wiktor |
| 4,893,623 A | 1/1990 | Rosenbluth |
| 4,911,713 A | 3/1990 | Sauvage et al. |
| 4,911,716 A | 3/1990 | Blom et al. |
| 4,913,141 A | 4/1990 | Hillstead |
| 4,919,133 A * | 4/1990 | Chiang ........................ 606/159 |
| 4,921,484 A | 5/1990 | Hillstead |
| 4,921,499 A | 5/1990 | Hoffman et al. |
| 4,922,905 A | 5/1990 | Strecker |
| 4,926,860 A | 5/1990 | Stice et al. |
| 4,934,380 A | 6/1990 | de Toledo |
| 4,950,258 A | 8/1990 | Kawai et al. |
| 4,954,126 A | 9/1990 | Wallsten |
| 4,955,384 A | 9/1990 | Taylor et al. |
| 4,955,863 A | 9/1990 | Walker et al. |
| 4,969,458 A | 11/1990 | Wiktor |
| 4,990,155 A | 2/1991 | Wilkoff |
| 4,994,069 A | 2/1991 | Ritchart et al. |
| 4,994,071 A | 2/1991 | MacGregor |
| 4,998,923 A | 3/1991 | Samson et al. |
| 5,003,989 A | 4/1991 | Taylor et al. |
| 5,019,040 A * | 5/1991 | Itaoka et al. ................. 604/95 |
| 5,019,090 A | 5/1991 | Pinchuk |
| 5,035,712 A | 7/1991 | Hoffman |
| 5,037,427 A | 8/1991 | Harada et al. |
| 5,041,126 A | 8/1991 | Gianturco |
| 5,057,092 A | 10/1991 | Webster, Jr. |
| 5,057,114 A | 10/1991 | Wittich et al. |
| 5,059,211 A | 10/1991 | Stack et al. |
| 5,061,275 A | 10/1991 | Wallsten et al. |
| 5,061,285 A | 10/1991 | Koch |
| 5,064,428 A | 11/1991 | Cope et al. |
| 5,064,435 A | 11/1991 | Porter .......................... 623/12 |
| 5,067,957 A | 11/1991 | Jervis |
| 5,071,407 A | 12/1991 | Termin et al. |
| 5,078,726 A | 1/1992 | Kreamer |
| 5,078,736 A | 1/1992 | Behl |
| 5,100,429 A | 3/1992 | Sinofsky et al. |
| 5,102,417 A | 4/1992 | Palmaz |
| 5,108,420 A | 4/1992 | Marks |
| 5,123,917 A | 6/1992 | Lee |
| 5,129,883 A | 7/1992 | Black |
| 5,133,732 A | 7/1992 | Wiktor |
| 5,135,536 A | 8/1992 | Hillstead |
| 5,147,370 A | 9/1992 | McNamara et al. |
| 5,154,725 A | 10/1992 | Leopold |
| 5,167,614 A | 12/1992 | Tessmann et al. |
| 5,171,314 A | 12/1992 | Dulebohn |
| 5,176,664 A | 1/1993 | Weisman |
| 5,183,085 A | 2/1993 | Timmermans |
| 5,189,110 A | 2/1993 | Ikematu et al. |
| 5,190,546 A | 3/1993 | Jervis |
| 5,197,978 A * | 3/1993 | Hess ............................ 623/1 |
| 5,201,901 A | 4/1993 | Harada et al. |
| 5,211,658 A | 5/1993 | Clouse |
| 5,217,483 A | 6/1993 | Tower |
| 5,224,953 A | 7/1993 | Morgentaler |
| 5,231,989 A | 8/1993 | Middleman et al. |
| 5,238,005 A | 8/1993 | Imran |
| 5,241,970 A | 9/1993 | Johlin, Jr. et al. |
| 5,242,399 A | 9/1993 | Lau et al. |
| 5,242,448 A | 9/1993 | Pettine et al. |
| 5,242,451 A | 9/1993 | Harada et al. |
| 5,246,445 A | 9/1993 | Yachia et al. |
| 5,261,878 A | 11/1993 | Galindo |
| 5,275,622 A | 1/1994 | Lazarus et al. |
| 5,282,824 A | 2/1994 | Gianturco |
| 5,292,331 A | 3/1994 | Boneau |
| 5,304,200 A | 4/1994 | Spaulding |
| 5,314,472 A | 5/1994 | Fontaine |
| 5,354,308 A | 10/1994 | Simon et al. |
| 5,354,309 A | 10/1994 | Schnepp-Pesch et al. |
| 5,366,504 A | 11/1994 | Andersen et al. ............. 623/11 |
| 5,383,892 A | 1/1995 | Cardon et al. ............... 606/198 |
| 5,423,849 A * | 6/1995 | Engelson et al. ............ 606/191 |
| 5,449,373 A | 9/1995 | Pinchasik et al. ........... 606/198 |
| 5,478,349 A | 12/1995 | Nicholas ...................... 606/198 |
| 5,545,210 A | 8/1996 | Hess et al. .................... 623/1 |
| 5,562,641 A | 10/1996 | Flomenblit et al. .......... 604/281 |
| 5,601,593 A | 2/1997 | Freitag ......................... 606/198 |
| 5,674,277 A | 10/1997 | Freitag ........................... 623/1 |

FOREIGN PATENT DOCUMENTS

| | | |
|---|---|---|
| EP | 0 536 164 B1 | 3/1994 |
| EP | 0 433 447 B1 | 6/1994 |
| FR | 2 248 303 | 10/1974 |
| JP | (A) 57-89859 | 6/1982 |
| JP | (A) 53-501458 | 9/1983 |
| JP | (A) 60-55964 | 4/1985 |
| JP | (A) 60-220030 | 11/1985 |
| JP | (A) 61-6655 | 1/1986 |
| JP | (B2) 61-6655 | 2/1986 |
| JP | (A) 61-220648 | 9/1986 |
| JP | (A) 62-82975 | 4/1987 |

| | | | | | | |
|---|---|---|---|---|---|---|
| JP | (A) 62-82976 | 4/1987 | | WO | WO 92/19310 | 11/1992 |
| WO | WO 83/00997 | 3/1983 | | WO | WO92/22263 | 12/1992 |
| WO | WO 83/03752 | 11/1983 | | WO | WO 93/13824 | 7/1993 |
| WO | WO 89/02755 | 4/1989 | | WO | WO 93/19803 | 10/1993 |
| WO | WO 89/03197 | 4/1989 | | WO | WO94/06732 | 3/1994 |
| WO | WO 89/08433 | 9/1989 | | WO | WO 94/12136 | 6/1994 |
| WO | WO 91/07928 | 6/1991 | | WO | WO 95/31945 | 11/1995 |
| WO | WO 91/16005 | 10/1991 | | | | |
| WO | WO 92/06734 | 4/1992 | | * cited by examiner | | |

Fig. 4a (LAYER 32)
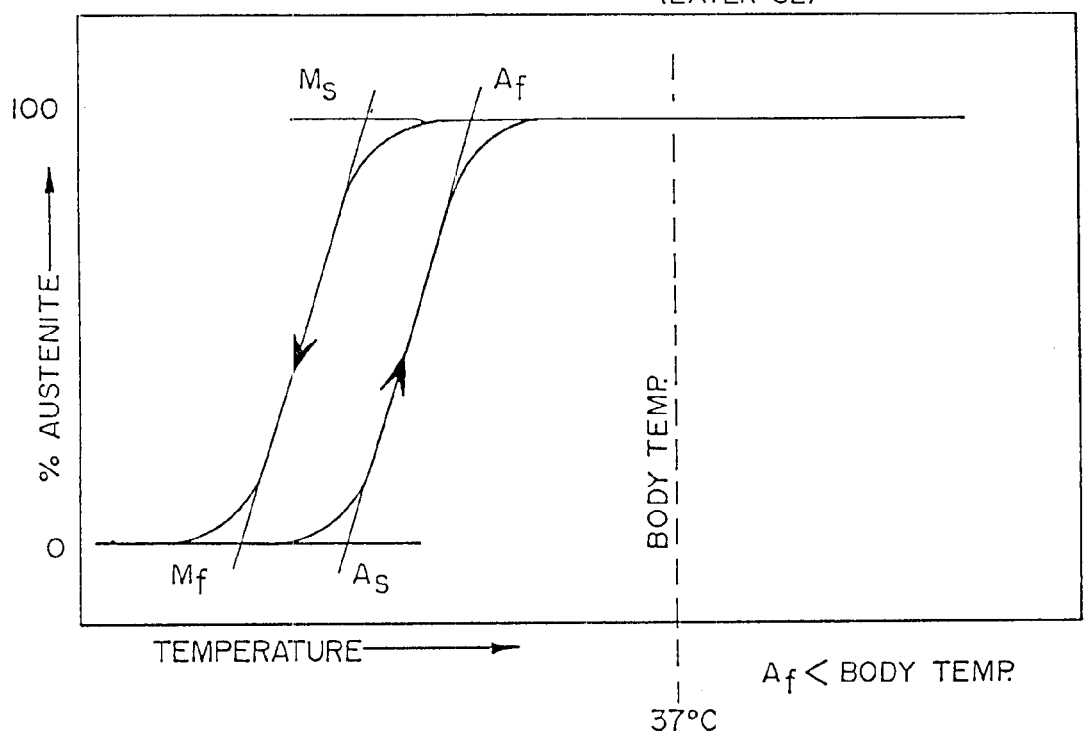
Fig. 4b (LAYER 34)
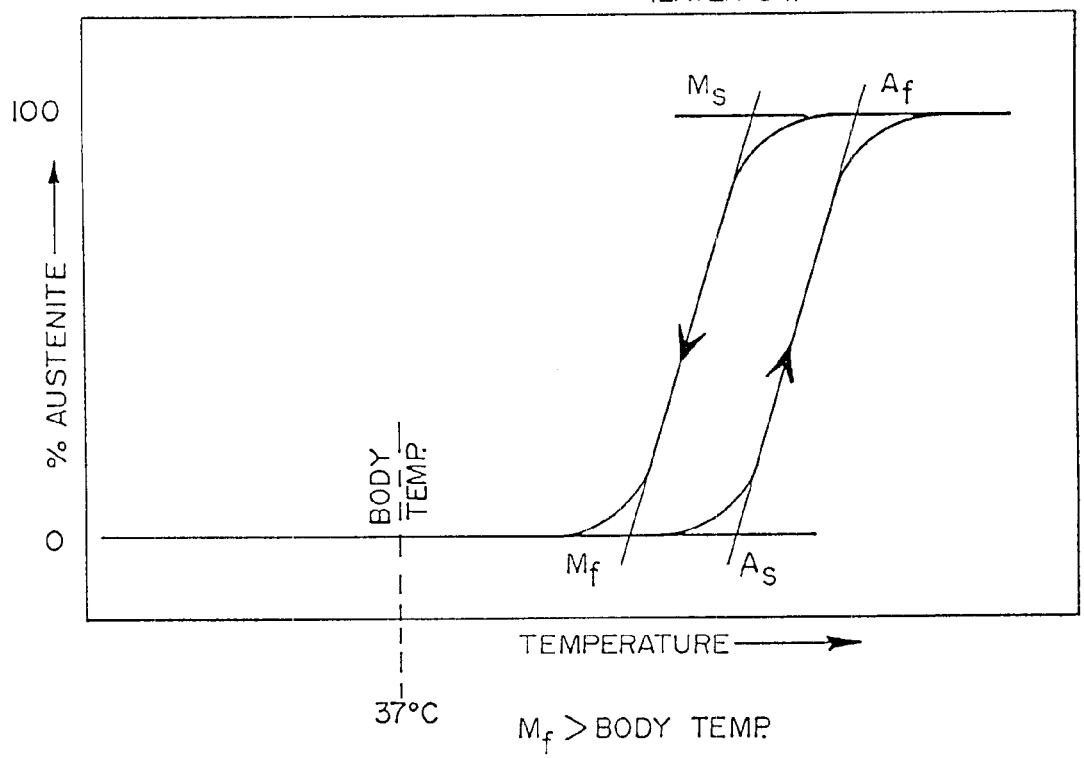

TISSUE SUPPORTING DEVICES

CROSS REFERENCE TO RELATED APPLICATIONS

This application is a divisional of U.S. patent application Ser. No. 08/737,492 filed Mar. 19, 1997, a National Stage application based on PCT/US95/06228 filed May 18, 1995 claiming priority of U.S. application Ser. No. 08/246,320 filed May 19, 1994, now abandoned. U.S. application Ser. No. 08/737,492 and PCT/US95/06228 are also Continuation-in-Part applications of application Ser. No. 08/246,320, now abandoned. All of the applications referred to in this paragraph are incorporated herein by references.

BACKGROUND OF THE INVENTION

This invention relates to tissue supporting devices in general and most particularly to vascular stents for placement in blood vessels. A primary feature of the devices of this invention is that they are expandable within the body.

In the past, such devices have been provided for implantation within body passageways. These devices have been characterized by the ability to be enlarged radially, often having been introduced into the desired position in the body as by percutaneous techniques or surgical techniques.

These devices are either expanded mechanically, such as by expansion of a balloon positioned inside the device, or are capable of releasing stored energy to self-expand themselves within the body.

The materials which have been used to make up these devices have included ordinary metals, shape memory alloys, various plastics, both biodegradable and not, and the like.

This invention is concerned with the use of these materials in a new multiple component arrangement which allows for initial self-expansion and subsequent deformation to a final enlarged diameter in the body.

Balloon expandable stents do not always expand uniformly around their circumference. As a result, healing may not take place in a consistent manner. If the stent is coated or covered, non-uniform expansion may tear the covering or coating. Additionally, long stents of this type may require long balloons which can be difficult to handle, difficult to size, and may not offer ideal performance in tortuous passages in blood vessels and the like.

Thus, when addressing such issues, self-expandable stents have been thought to be generally more desirable. Unfortunately, one cannot control the degree of expansion and hence the degree of embedment in the vessel wall. It has been determined that a stent must be embedded to some degree to be clinically satisfactory.

The stents of the present invention provide the best features of both of these types of stents without their drawbacks.

SUMMARY OF THE INVENTION

The tissue supporting devices of this invention are generally cylindrical or tubular in overall shape and of such a configuration as to allow radial expansion for enlargement. They are often referred to herein in the general sense as "stents". Furthermore, the devices are comprised of at least one component, element, constituent or portion which exhibits a tendency to self-expand the device to an expanded size and at least one other component, element, constituent or portion which is deformable so as to allow an external force, such as a balloon positioned within the body of the device, to further expand it to a final, larger desired expanded size. The terms "component", "element", "constituent" and "portion" are often referred to herein collectively as "portion".

Preferably, the devices of the invention are made of metal and most preferably of shape memory alloys.

In one embodiment, a first portion is a resilient spring-like metal for self-expansion and a second portion is a deformable metal for final sizing. In a more preferred shape memory embodiment, a first portion is a self-expanding austenitic one and a second is a martensitic one capable of deformation. In the case of shape memory embodiments the "portions" may be discrete or merely different phases of an alloy.

The most preferred embodiment of the invention is a stent, preferably of shape memory alloy. The most preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, Cu—Zn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art.

The invention will be specifically described hereinbelow with reference to stents, a preferred embodiment of the invention although it is broadly applicable to tissue support devices in general.

BRIEF DESCRIPTION OF THE FIGURES

FIGS. 4a and 4b are graphs showing the martensitic/austenitic temperature transformation curves of the layers in the stent of FIG. 3.

FIGS. 8–11 show various expandable configurations (closed and open) illustrated in fragment which may be used in the stents of this invention.

DETAILED DESCRIPTION OF THE INVENTION

Preferred embodiments of this invention are described below with particular reference to the accompanying drawing Figures.

Figure 1:
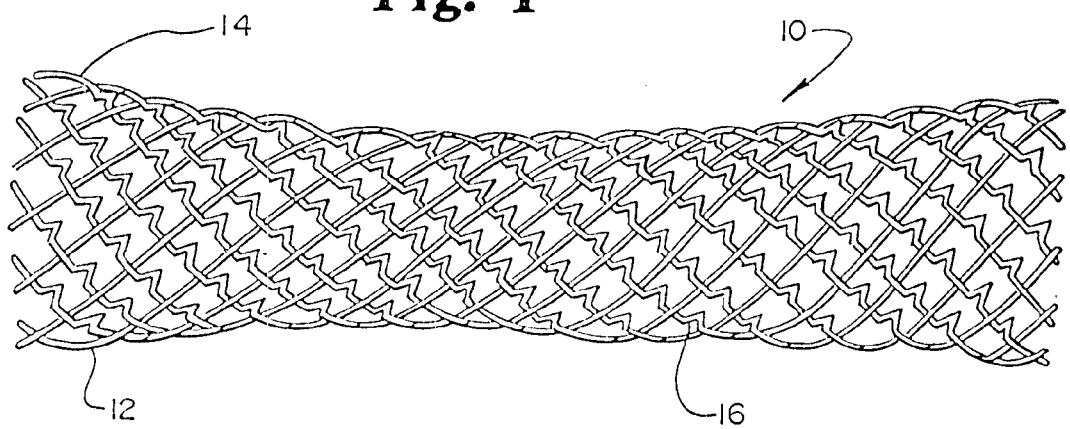
FIG. 1 is a braided stent according to one embodiment of this invention.

Referring first to the embodiment shown in FIG. 1, a stent 10 is shown comprised of braided or interwoven metal strands 12 and 14. Strands 12 are of a resilient spring-like metal such as spring steel, Elgiloy for example. Preferably, strands 12 are spirally extending in the same direction, spiraling to the right as seen in FIG. 1. Strands 14 are of a deformable or annealed metal such as stainless steel and are preferably spiraled in the opposite direction as strands 12, as shown in FIG. 1.

Given such a stent construction of two components i.e., strands 12 and 14, it can be seen that stent 10 may be readily loaded on a catheter as by placing it over an uninflated balloon on a balloon catheter and compressing it tightly around the balloon and then placing a sheath over the stent to hold it in place during the transluminal placement procedure. Once in place, the sheath is removed, for example slid back, to expose the stent, allowing it to self-expand by force of the resilient strands 12 to substantially assume a self-expanded shape/size. Some self-expansion may be restrained if held back by strands 14. To finally adjust the size of the stent, the balloon may be expanded by inflation from within the stent to exert an outward radial force on the stent and further enlarge it by stretching and deforming the deformable metal of strands 14. This may be aided by building into strands 14, a series of readily deformable structures or means such as bends or kinks 16 as shown in FIG. 1. It can be seen that a permanent adjustable size beyond the self-expanded size may be obtained with this embodiment. It is to be noted that many configurations other than braided may be readily devised to take advantage of this two component concept, including various of the subsequent configurations described hereinbelow. Also, it should be noted that, although not preferred, the stent may be initially deployed without a balloon; the balloon following on a separate catheter.

Referring now to subsequent features, other preferred embodiments of the invention will be described which make use of shape memory alloys and some of their unique properties, primarily their special types of deformation i.e., shape memory deformation in martensite and/or superelastic deformation in austenite.

The term "superelasticity" is used to describe the property of certain shape memory alloys to return to their original shape upon unloading after a substantially deformation while in their austenitic state. Superelastic alloys can be strained while in their austenitic state more than ordinary spring materials without being plastically deformed. This unusually large elasticity in the austenitic state is also called "pseudoelasticity", because the mechanism is nonconventional in nature, or is also sometimes referred to as "transformational superelasticity" because it is caused by a stress induced phase transformation. Alloys that show superelasticity also undergo a thermoelastic martensitic transformation which is also the prerequisite for the shape memory effect. Superelasticity and shape memory effects are therefore closely related. Superelasticity can even be considered part of the shape memory effect.

The shape memory and superelasticity effects are particularly pronounced in Ni—Ti alloys. This application will therefore focus on these alloys as the preferred shape memory alloys. The shape memory effect in Ni—Ti alloys has been described many times and is well known.

In near-equiatomic Ni—Ti alloys, martensite forms on cooling from the body centered cubic high temperature phase, termed austenite, by a shear type of process. This martensitic phase is heavily twinned. In the absence of any externally applied force transformation takes place with almost no external macroscopic shape change. The martensite can be easily deformed by a "flipping over" type of shear until a single orientation is achieved. This process is also called "detwinning".

If a deformed martensite is now heated, it reverts to austenite. The crystallographic restrictions are such that it transforms back to the initial orientation thereby restoring the original shape. Thus, if a straight piece of wire in the austenitic condition is cooled to form martensite it remains straight. If it is now deformed by bending, the twinned martensite is converted to deformed martensite. On heating, the transformation back to austenite occurs and the bent wire becomes straight again. This process illustrates the shape memory deformation referred to above.

The transformation from austenite to martensite and the reverse transformation from martensite to austenite do not take place at the same temperature. A plot of the volume fraction of austenite as a function of temperature provides a curve of the type shown schematically in FIG. 2. The complete transformation cycle is characterized by the following temperatures: austenite start temperature ($A_s$), austenite finish temperature ($A_f$), both of which are involved in the first part (1) of an increasing temperature cycle and martensite start temperature ($M_s$) and martensite finish temperature ($M_f$), both of which are involved in the second part (2) of a decreasing temperature cycle.

Figure 2:
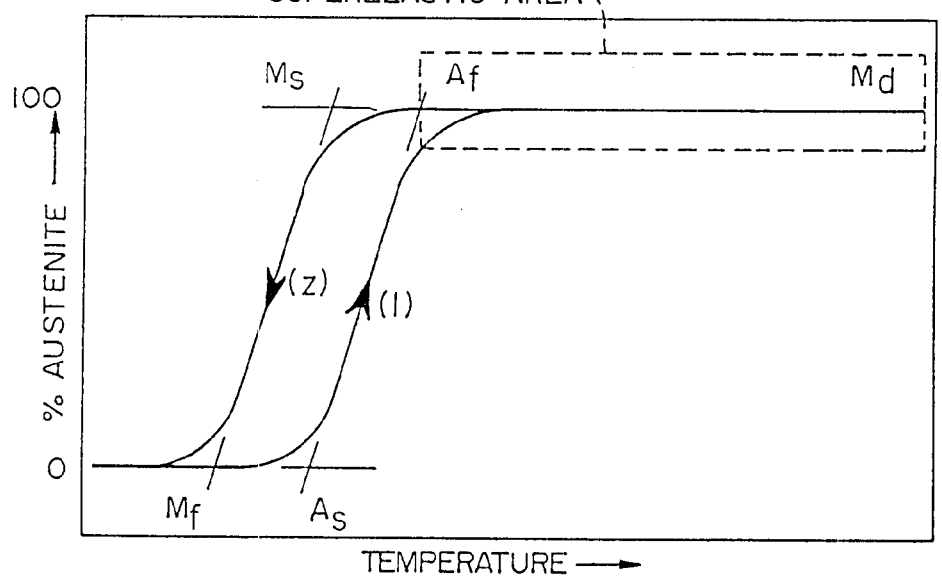
FIG. 2 is a graph showing the martensitic/austenitic temperature transformation curve and the superelastic area of a shape memory alloy.

FIG. 2 represents the transformation cycle without applied stress. However, if a stress is applied in the temperature range between $A_s$ and $M_d$, martensite can be stress-induced. Stress induced martensite is deformed by detwinning as described above. Less energy is needed to stress induce and deform martensite than to deform the austenite by conventional mechanisms. Up to about 8% strain can be accommodated by this process (single crystals of specific alloys can show as much as about 25% pseudoelastic strain in certain directions). As austenite is the thermodynamically stable phase at temperatures between $A_s$ and $M_d$ under no-load conditions, the material springs back into its original shape when the stress is no longer applied.

It becomes increasingly difficult to stress-induce martensite at increasing temperatures above $A_f$. Eventually, it is easier to deform the material by conventional mechanisms (movement of the dislocation, slip) than by inducing and deforming martensite. The temperature at which martensite can no longer be stress-induced is called $M_d$. Above $M_d$, Ni—Ti alloys are deformed like ordinary materials by slipping.

Additional information regarding shape memory alloys is found in the following references, all of which are incorporated fully herein by reference:

"Super Elastic Nickel-Titanium Wires" by Dieter Stöckel and Weikang Yu of Raychem Corporation, Menlo Park, Calif., copy received November 1992;

Metals Handbook, Tenth Edition, Vol. 2, Properties and Selection: Nonferrous Alloys and Special-Purpose Materials, "Shape Memory Alloys" by Hodgson, Wu and Biermann, pp. 897–902; and, In Press, Titanium Handbook, ASM (1994), Section entitled "Structure and Properties of Ti—Ni Alloys by T. W. Duerig and A. R. Pelton.

Since the most preferred shape memory alloy is Ni—Ti, the martensitic state of this alloy may be used to advantage in the two component concept of this invention.

Figure 3:
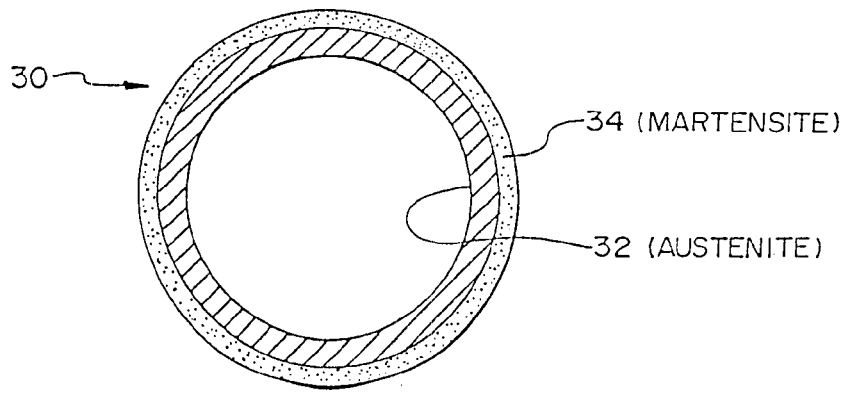
FIG. 3 is an end view of a layered stent having two discrete components according to one aspect of this invention.
Figure 5A:
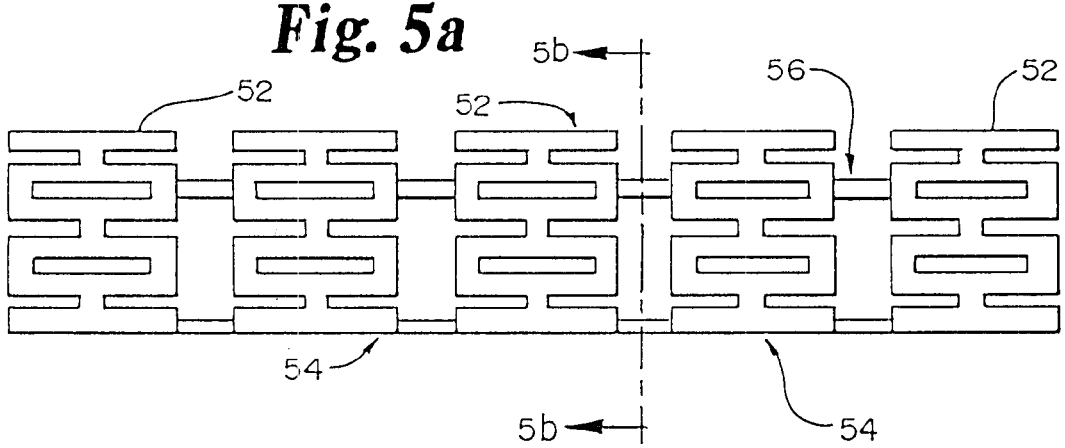
FIGS. 5a and 5b are views of another embodiment of the invention comprised of alternating rings of shape memory alloy.
Figure 5B:
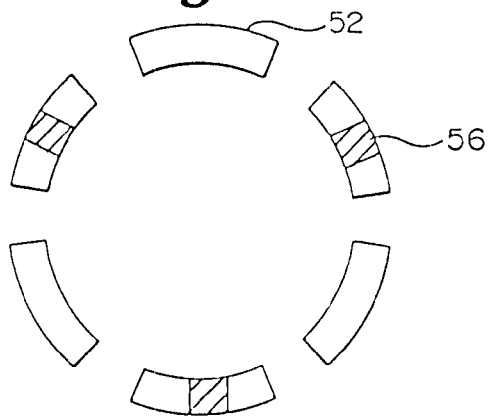
Figure 6:
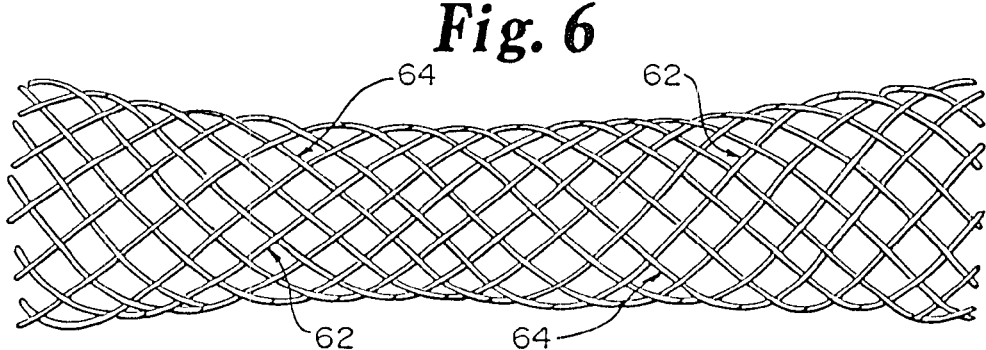
FIG. 6 is a showing of a stent fragment of a braided version of a shape memory stent of this invention.

For example, with reference to FIG. 3, a layered construction may be provided in a stent 30 (shown in end view) which is generally a hollow cylindrical or tubular body in shape but which may be formed in a wide variety of specific configurations or patterns to foster radial expansion of the body as exemplified in FIGS. 1, 5, 6 and in subsequent FIGS. 8–11.

Stent 30 is comprised of at least two layers 32 and 34, one of which 32 is a Ni—Ti alloy (50.8 atomic wt. % Ni, balance Ti, transition temperature of A=0° C.) and normally in the austenitic state, the other of which 34 is a Ni—Ti (49.4 atomic wt. % Ni, balance Ti, transition temperature $A_f$=60° C.) and normally in the martensitic state. Preferably, the inner layer is 32 and the outer layer is 34. However, this may be reversed and also a plurality of layers, alternating or otherwise, may be utilized in this particular embodiment.

Stent 30 is made to a fabricated size and shape (parent shape) which provides austenitic layer 32 its parent shape and size i.e., its superelastic high temperature shape and size. Obviously, in its as fabricated condition, the Ni—Ti alloy of austenitic layer 32 is selected so as to have a transition temperature range between its austenitic and martensitic states which is lower than body temperature as to ensure that in the body and at body temperatures the austenitic state will always prevail.

On the other hand, martensitic layer 34 is of a Ni—Ti alloy having a transition temperature range significantly greater than body temperature so as to ensure that under body conditions the martensitic state will always prevail and the alloy will never transform to austenite in stent use. This is shown in the graphs of FIGS. 4a and 4b which demonstrate the relative transition temperatures of layers 32 and 34, respectively for purposes of this invention. It can be seen from these graphs that the normal condition of layer 32 (FIG. 4a) at body temperatures and higher is the austenitic state while the normal condition of layer 34 (FIG. 4b) at body temperatures is martensitic.

To manufacture the layered construction, one may make the austenitic portion with any standard metallurgical technique and vapor deposit the martensitic portion on its surface. Other manufacturing techniques such as diffusion bonding, welding, ion beam deposition, and various others will be apparent to those familiar with this art.

Such a stent may be compressed or constrained (deformed to a small diameter) onto a balloon catheter as described for the previous embodiment and captured within a sheath. During the constrainment, austenitic layer 32 may stress induce to a martensitic state. In the alternative, the stent may be cooled below the transition temperature of layer 32 to facilitate its deformation and constrainment. Martensitic layer 34 merely undergoes deformation. Thus the stent may be "loaded" onto a balloon catheter. However, with temperature changes occurring up to body temperature, layer 32 will remain martensite until the constraint is removed. When released in place in the body, stent 30 will expand to a percentage of its self-expanded size and shape due to the transformation of layer 32 from martensite to austenite at which point the balloon may be used to radially expand the stent to a greater permanent diameter by deforming martensitic layer 34. On the other hand, initial deployment can take place without a balloon which may be separately inserted after deployment.

The two component concept of the invention in the layered embodiment of FIG. 3 requires both the martensitic and austenitic phase characteristics of shape memory alloy (s) in the two discrete components 32 and 34.

Preferably, the stent is fabricated in such a way that the austenitic layer 32 tends to self-expand stent 30 to a predetermined fabricated diameter (parent shape). The martensitic layer 34 tends to hold back this self-expansion, preventing full expansion. For example, the stent may only be able to self-expand to 75% of its full possible diameter (as determined by the austenitic layer). Therefore, expansion beyond 75% is accomplished by an applied external force, as by the balloon inside the stent. It is suggested that the stent not be expanded beyond its normal fabricated diameter for the austenitic layer 32 will have the tendency of making the stent diameter smaller as it tries to recover its fabricated diameter (parent shape). If the stent is subjected to a temperature above body temperature and above the transition temperature of the martensitic layer (which is clinically unlikely), the stent will self-expand to the fabricated diameter only. Depending on design size there are thus provided permanent stents capable of fulfilling any needed range of sizes with an adjustable sizing capability.

As is known in the art, the desired properties of the shape memory alloys required for use in this invention may be obtained by alloy composition and working and heat treatment of the alloys, in various combinations or singly.

Manufacturing techniques influence the phase characteristics of the material. Alloy composition, work history, and heat treatment all influence the final characteristics. At a specific operating temperature, say body temperature, the austenite phase material will have a transition temperature below body temperature (i.e., $A_f$=0° C.). The material is capable of taking high strains and recovering after the load is released. The martensite phase material will have a higher transition temperature than body temperature (i.e., $A_f$=60° C.), and is characteristically soft and pliable and retains the deformed shape after load removal. This martensite deformation is caused by detwinning, not the typical plastic deformation, or yielding, of crystal slip.

With reference to FIGS. 5 and 6, other stent constructions are shown which are similar to the layered version of FIG. 3 in so far as utilization of the two component concept of this invention is concerned.

FIGS. 5a and 5b shows a stent 50 made up of alternating expandable rings 52 and 54 of austenitic and martensitic alloys, respectively, analogous to layers 32 and 34 of the FIG. 3 embodiment. Rings 52 and 54 for example are interconnected by strut members 56 which may be of any material capable of rigidly holding the rings together. Other interconnector means may be used. As can be seen in FIG. 5b, the placement of strut members 56 does not require them to take part in the radial expansion of the stent and they can therefore be of a relatively ordinary material such as stainless steel.

Referring now to FIG. 6, a braided or interwoven construction is shown similar in construction to that of the embodiment of FIG. 1. In this embodiment, strands 62 extending to the right in FIG. 6 are an alloy in the austenitic state whereas strands 64 extending to the left in FIG. 6 are an alloy in the martensitic state.

Figure 7:
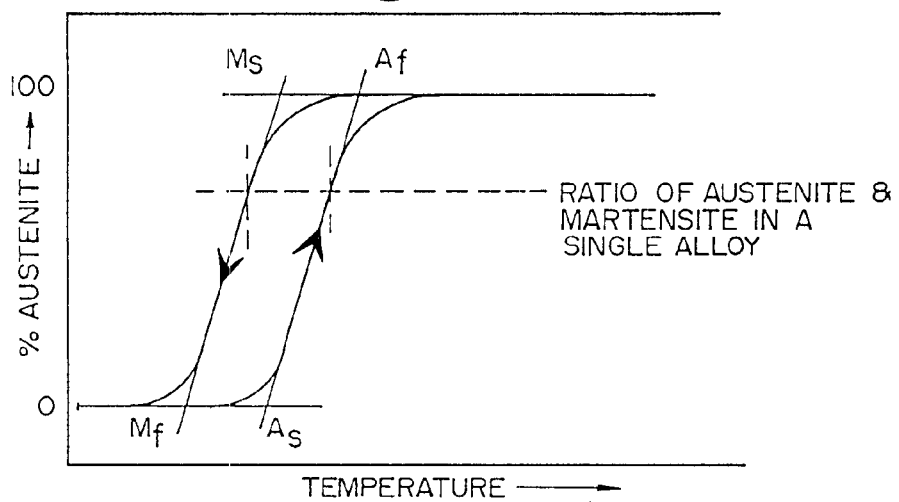
FIG. 7 is a graph showing a temperature window for a shape memory alloy to be used in yet another stent version of this invention.
Figure 8A:
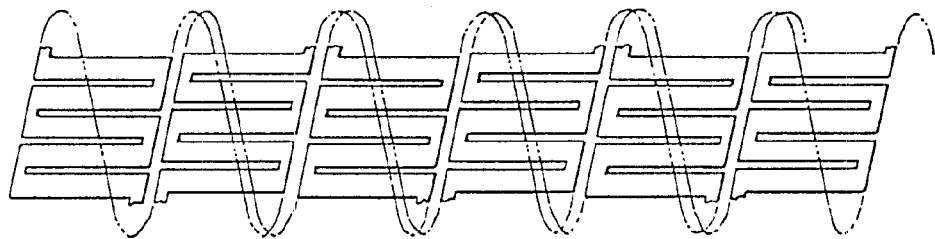
Figure 8B:
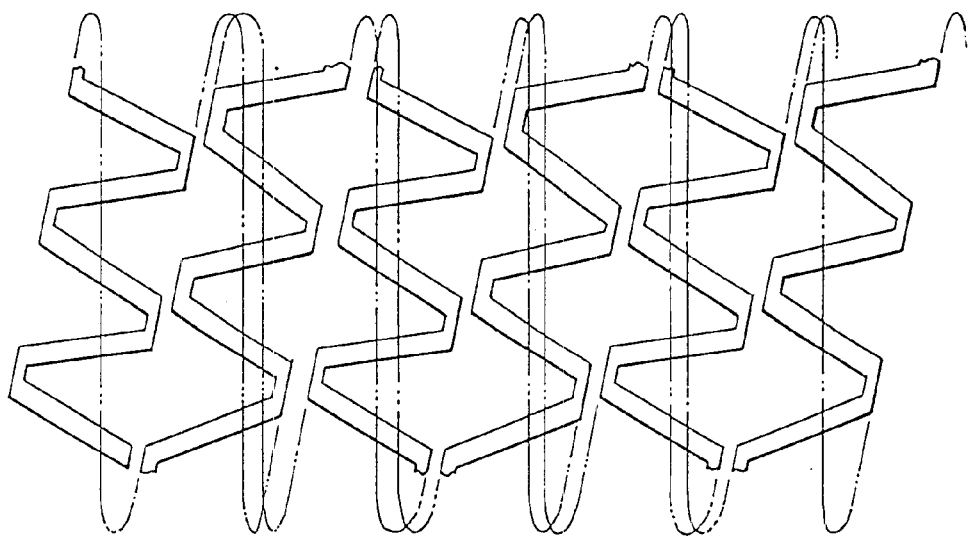

Referring now to the graph of FIG. 7, it is demonstrated that the two component concept of the invention may be embodied in two phases, i.e., components of a single shape memory alloy and need not be in the form of two discrete components such as layers, members, wires, etc. In the graph of FIG. 7, it can be seen that an alloy composition can be selected such that it has a phase transition temperature window that bounds the proposed operating temperatures of the stent, such as the normal body temperature range. Within this transitional window or zone, the material undergoes the phase transition and is effectively compositionally comprised of a ratio of austenitic to martensitic phase depending on the temperature of the stent. This ratio should be selected so as to provide sufficient radial force from the austenite phase while still allowing for further expansion of the martensite phase with a mechanical expansion means such as a balloon. Selecting body temperature as the operating temperature, a Ni—Ti alloy of about 50/50 atomic wt. % composition (range about 49/51%) will provide an acceptable "window" for this embodiment, the two components are the austenite and martensite phases of the nitinol.

The method of making a stent may be described as follows. Age the shape memory material (Ni Ti) until body temperature falls somewhere within the transformation window. Therefore the stent will not fully recover to its high temperature shape at body temperature. An example of this technique is described below.

A stent of tubular 50.8% Ni balance Ti was prepared having a 1.5 mm diameter. It was substantially all austenite at room temperature, the $A_f$ being about 15–20° C. and therefore being superelastic at room temperature. The stent was cooled to below room temperature to form substantially all martensite and mechanically expanded to 4.7 mm in diameter. It was maintained at the 4.7 mm in diameter and heat treated at 500° C. for 30 minutes and water quenched. Finally, it was again cooled to below room temperature to form substantially all martensite and compressed to a diameter of 1.5 mm. After deployment and at body temperature the stent has a diameter of 3.5 mm. At about 70% of full expansion, i.e., about 40° C. it had a diameter of 4.5 mm and at 42° C. it had a fully expanded diameter of 4.7 mm.

Figure 7A:
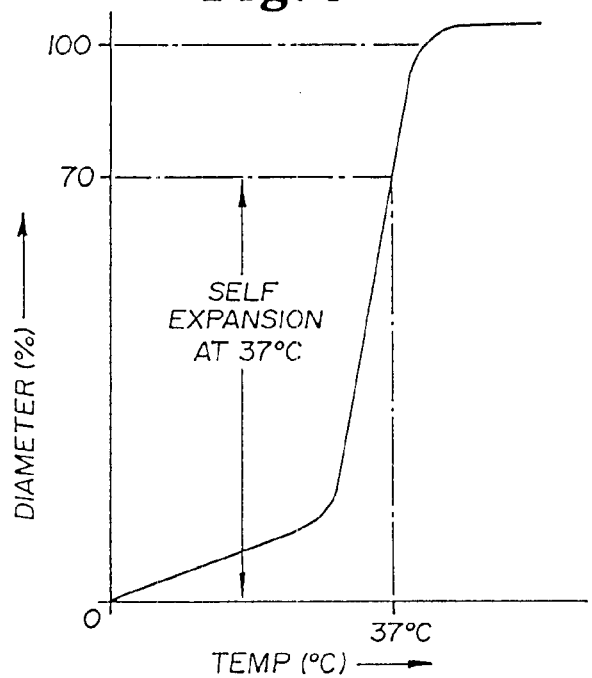
FIG. 7a is a graph showing expansion of a stent with temperature.

This method works fairly well, but due to the slope of the temperature versus diameter plot being extremely vertical at body temperature, a small change in body temperature, or manufacturing control, can have a large impact on the actual self expansion diameter. As can be seen from FIG. 7, the slope of the line between $A_f$ and $A_s$ is rather steep with small changes in temperature leading to large changes in percent austenite and consequently large changes in diameter of a stent made of such an alloy. FIG. 7a shows a temperature versus diameter plot. Three methods of modifying the slope of the line on the temperature versus diameter graph are cold work, pseudoelastic prestraining, and amnesia inducement, illustrated in FIGS. 7b, 7c and 7d, respectively.

Cold Work

Figure 7B:
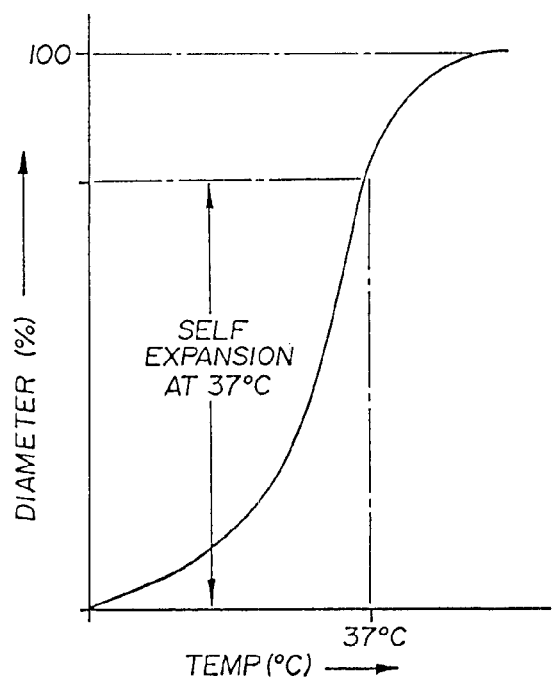
FIG. 7b is a graph of the same type, the stent having been coldworked.

Residual cold work in nitinol draws out or masks the point of $A_f$ on the diameter versus the temperature curve. This is seen by the sluggish increase in diameter as temperature increases in the last 20–30% of recover. By utilizing the effects of cold work, the effects of temperature change on diameter can be reduced in the last 20 to 30% of stent expansion. Shown in FIG. 7b is an example of a temperature versus diameter plot for a cold worked part. FIG. 7a above shows an example of a part without cold work.

Pseudoelastic Prestraining

Figure 7C:
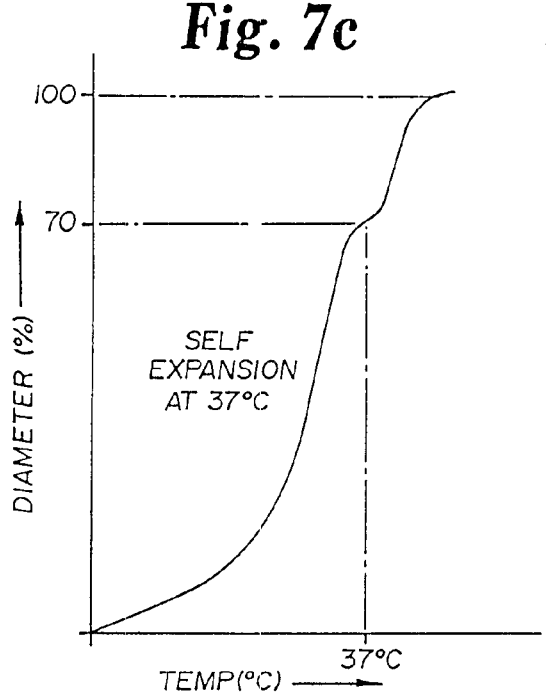
FIG. 7c is a graph of the same type, the stent having had pseudoelastic prestraining.

Utilizing the effects of pseudoelastic prestraining (S. Eucken and T. W. Duerig, *ACTA Metal*, Vol. 37, No. 8, pp 2245–2252, 1989) one can create two distinct plateaus in the stress-strain behavior. This difference in stress strain behaviors can be directly linked to two distinct $A_f$ temperatures for the two plateaus. By placing the transition between the two plateaus at the transition from self expanding to balloon expanding, i.e., 70%, one can control the characteristics of the stent at body temperature. The goal would be to place the $A_f$ temperature for the first plateau (from maximum compression to 70% expansion) below body temperature such that the stent has self expanding characteristics. The $A_f$ temperature for the second plateau would be above body temperature such that there is no additional self expansion in this region (70 to 100% expansion) a mechanical device, like a balloon, can then be used to custom size the stent between 70% and 100% of the high temperature shape. Results of such a technique is shown in FIG. 7c.

Amnesia Inducement

Figure 7D:
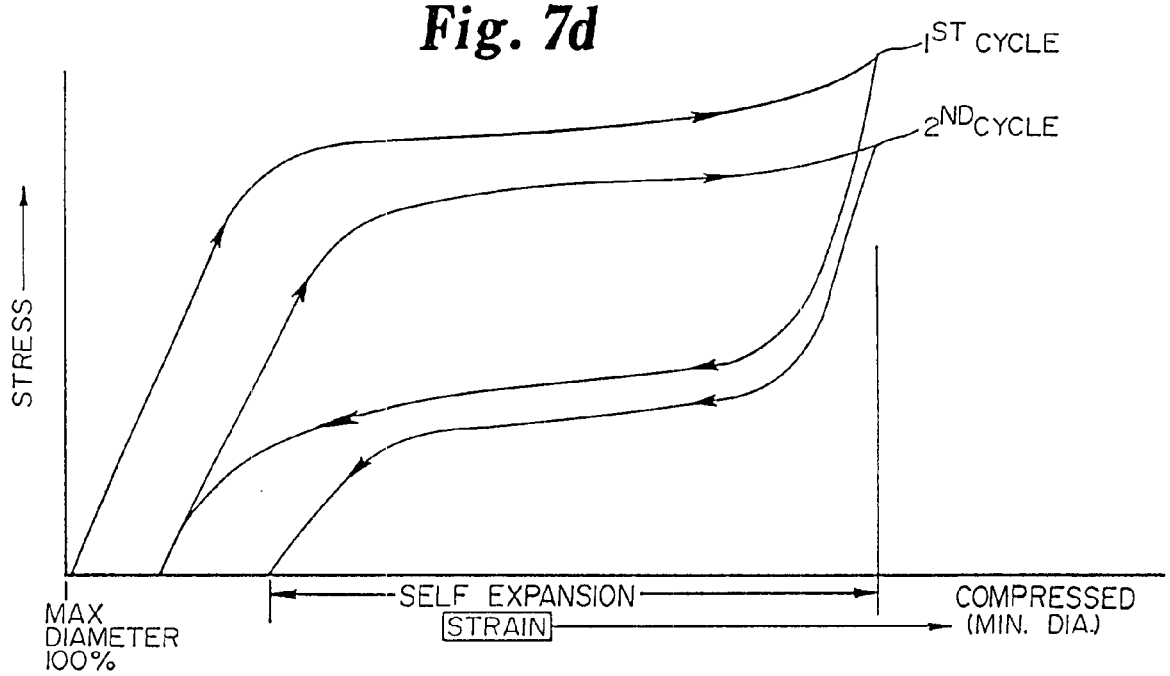
FIG. 7d is a graph of the same type, the stent having amnesia inducement.
Figure 9A:
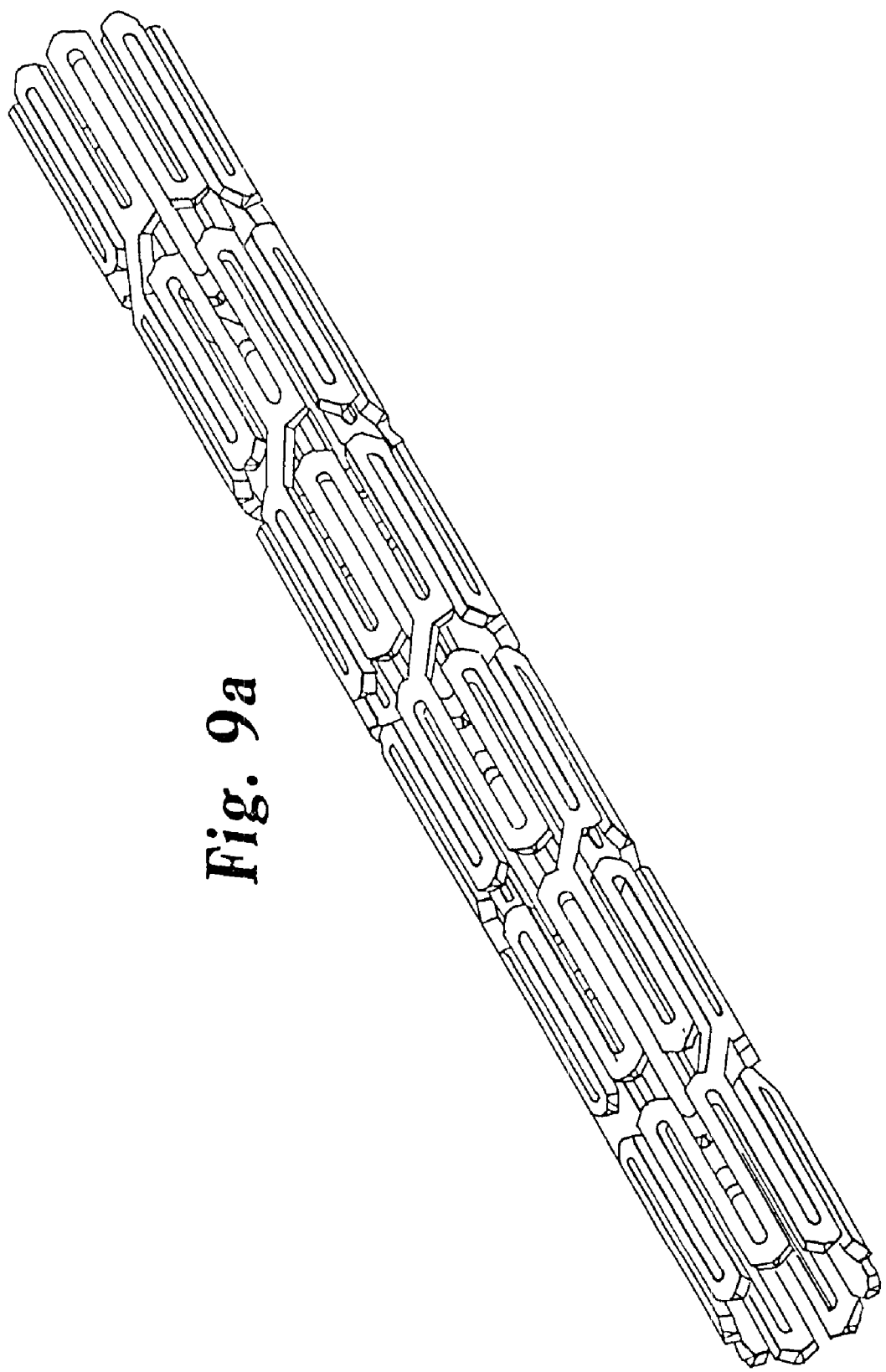
FIGS. 9a and 9b show a preferred embodiment of an articulated stent.
Figure 9B:
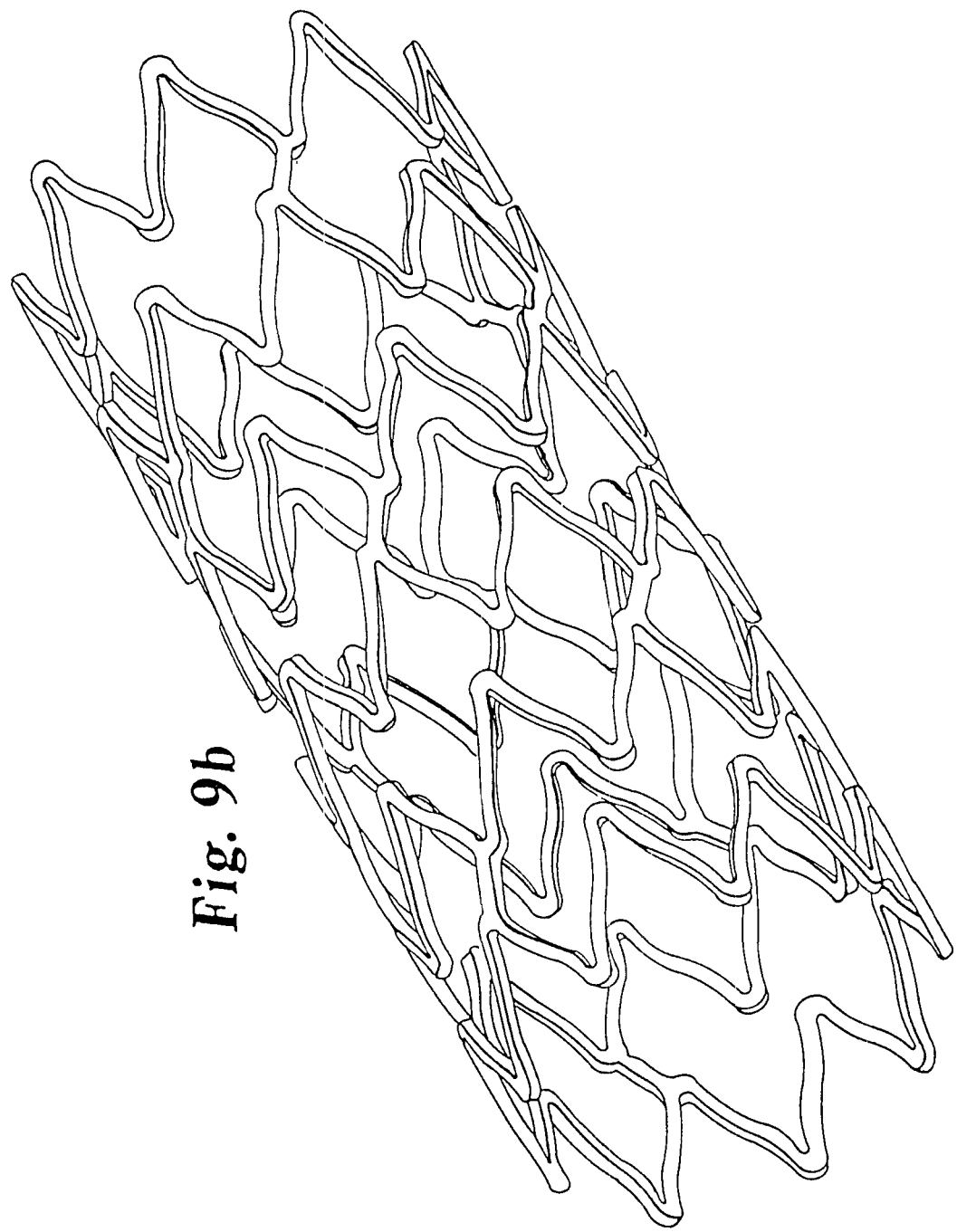
Figure 10A:
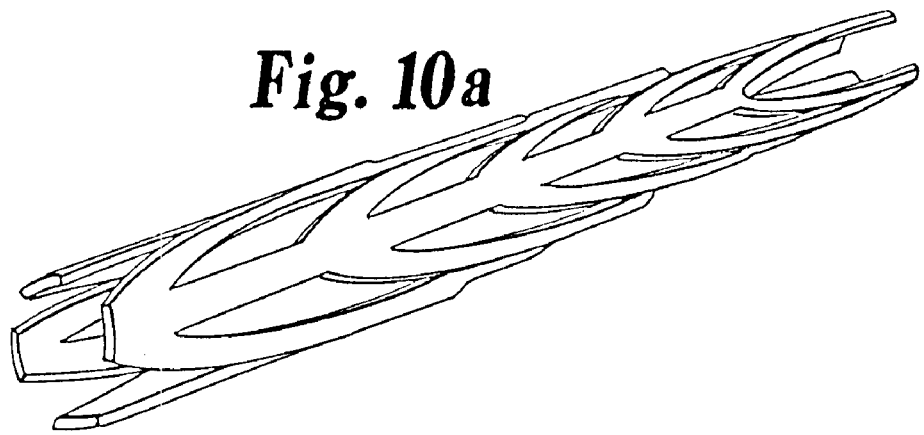
Figure 10B:
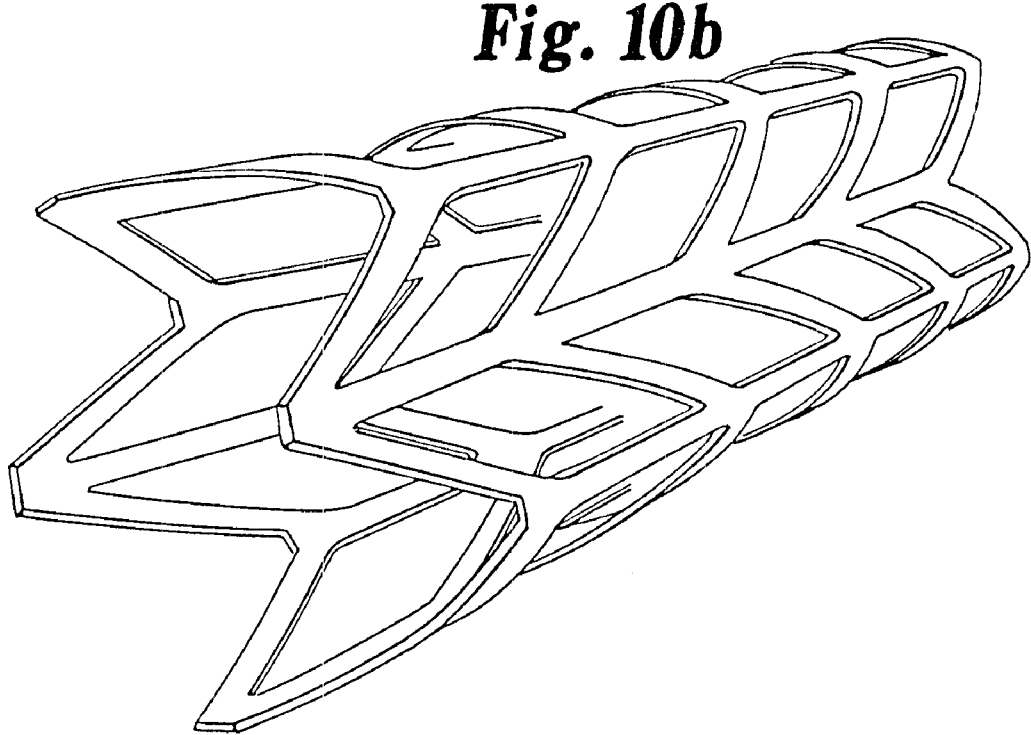
Figure 10C:
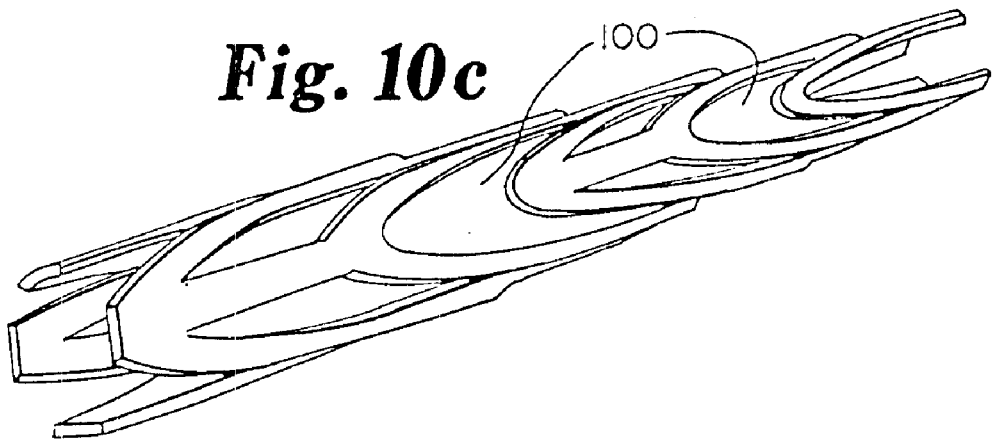
Figure 10D:
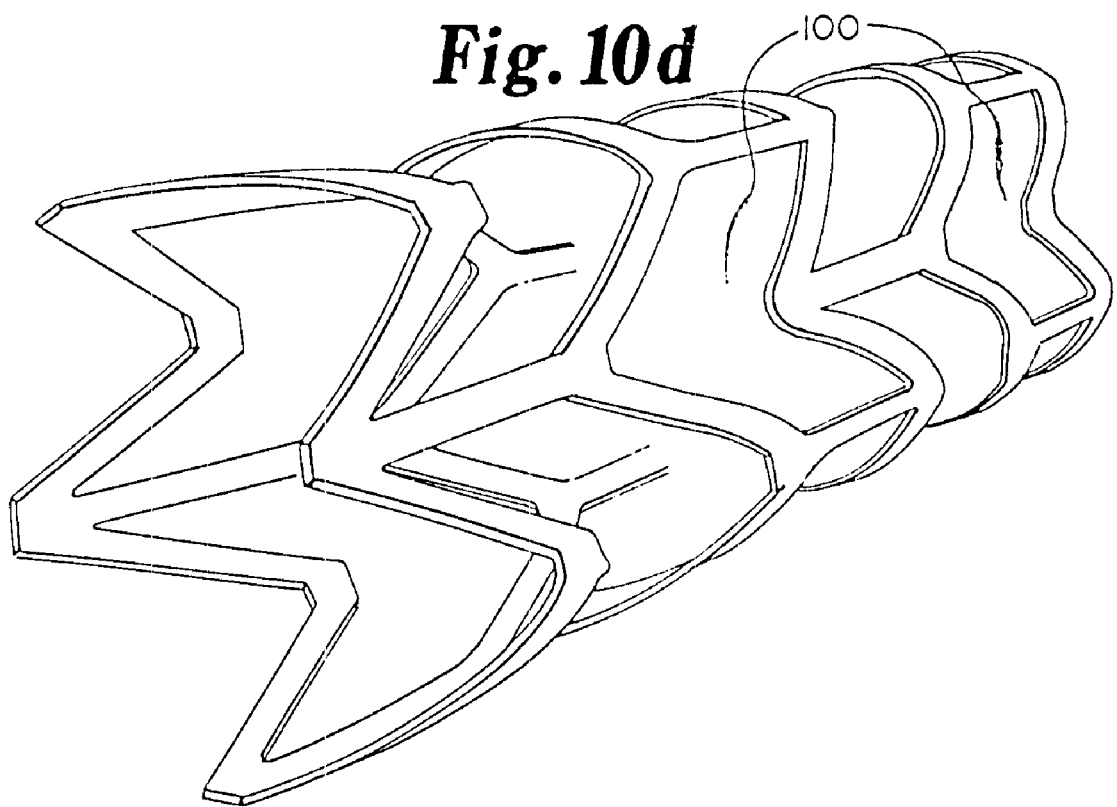
Figure 11A:
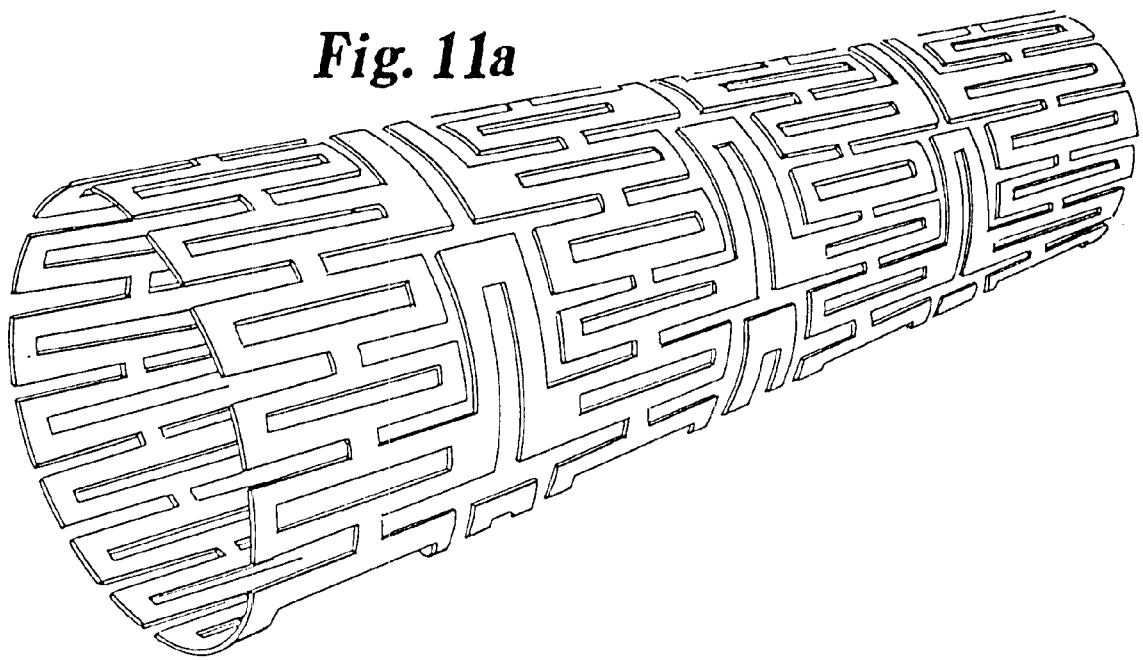
Figure 11B:
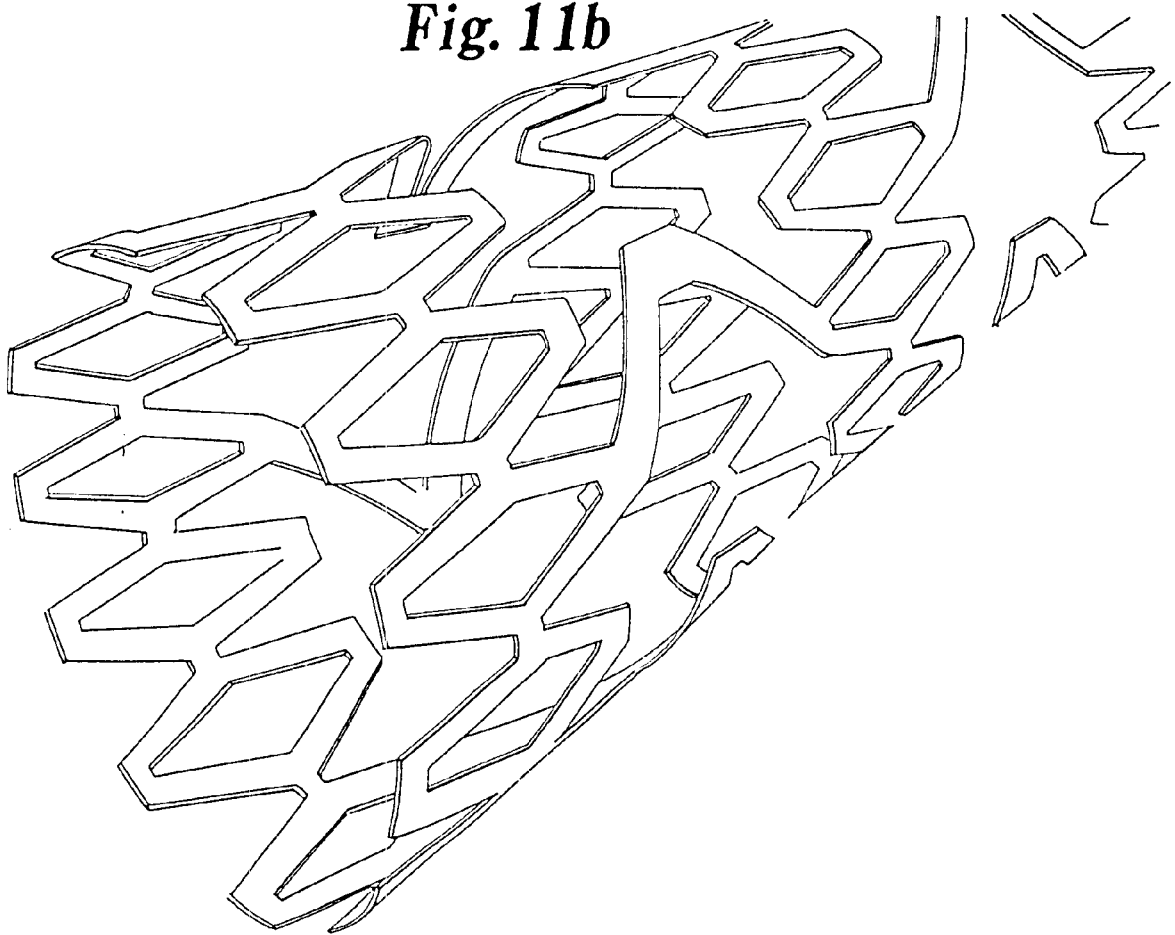

One of the characteristics of nitinol is cycle amnesia. This was also discussed about in the article referred to immediately above. As nitinol is cycled from its heat set shape as shown in FIG. 7d, there is an increase in the amount of amnesia to recover to the heat set shape with each cycle. As long as this amnesia is not caused by permanent plastic deformation, the amnesia can be removed by heating the part above $M_d$. This shows there is martensite left in the part after cycling which is preventing full recovery in the austenite phase (Oust above $A_f$). This presence of non recoverable martensite (below $M_d$) is what may be used for the balloon expansion region of the stent.

FIGS. 8–11 represent examples of various expandable configurations (a=closed, b=expanded) which may be incorporated into the devices of this invention. The version shown in FIGS. 10a and 10b may be modified as shown in FIGS. 10c and 10d (closed and open, respectively) by omitting portions (indicated at 100 in FIGS. 10c and 10d) as to render the stent flexible for articulation. This may be done to other of the structures as well to improve flexibility.

Figure 12:
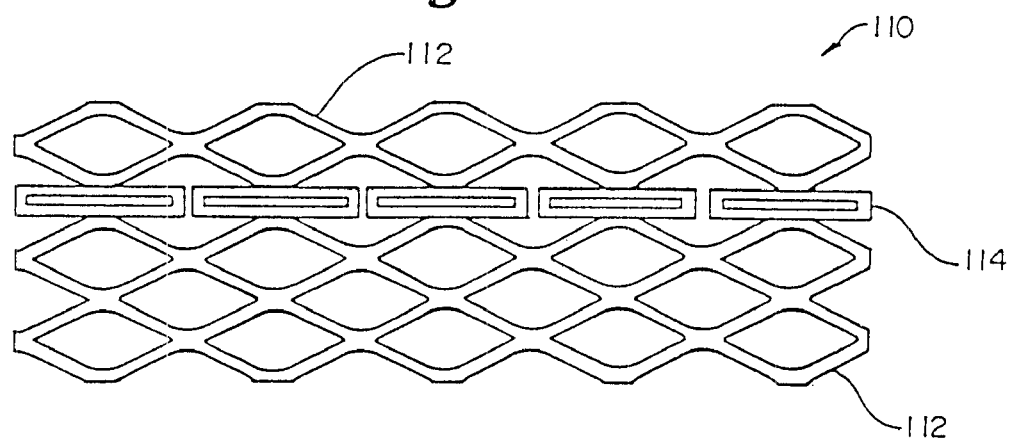
FIG. 12 shows another version of an expandable stent of the invention.

Yet another version of a device incorporating the two component concept of the invention is shown in FIG. 12. In this embodiment, a fragment of a stent 110 is shown. The stent includes a self-expanding component 112 and a deformable, external force expandable component 114. Self expanding component 112 may be resilient spring-like metal such a stainless steel or it may preferably be a shape memory alloy in the austenitic state. Component 114 may be any deformable metal or the like such as annealed stainless steel or preferably a shape memory alloy in the martensitic state. The two components may simply be mechanically, welded or bonded together. Functions and operations are as described hereinabove.

Figure 13:
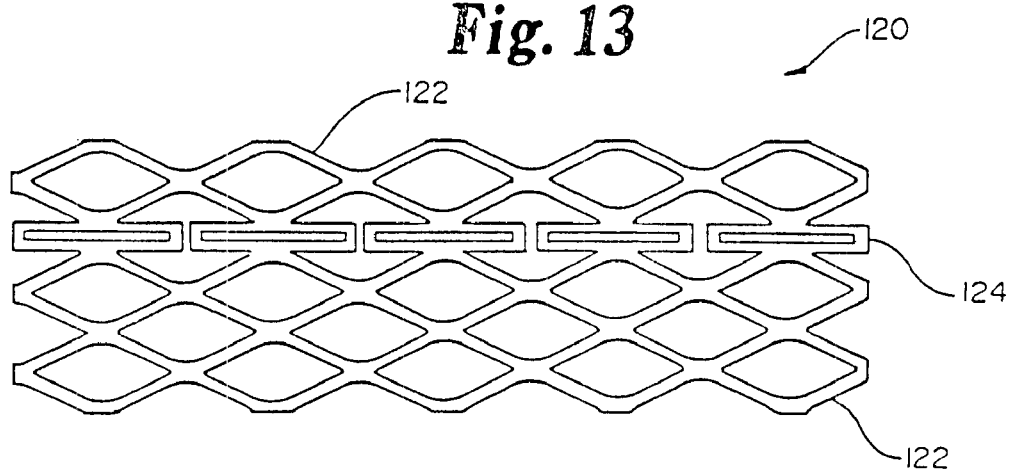
FIG. 13 shows yet another version of a stent which may be used with the invention.

Referring to FIG. 13 a version analogous to the embodiment of FIG. 12 is shown in which the two component concept is again embodied as different zones or portions of a single metal material.

As shown in FIG. 13, a stent 120 (fragment showing) is of a self-expanding component 122 and a deformable component 124, both of which may be a single metal as spring steel or austenitic Ni—Ti which has been appropriately treated with respect to component 124 as by localized heat treatment or the like to alter the characteristics of the material of the 122 component so as to render it deformable or martensitic, depending on whether it is merely resilient or is austenitic. Again, function and operation are the same as with other embodiments.

Figure 14:
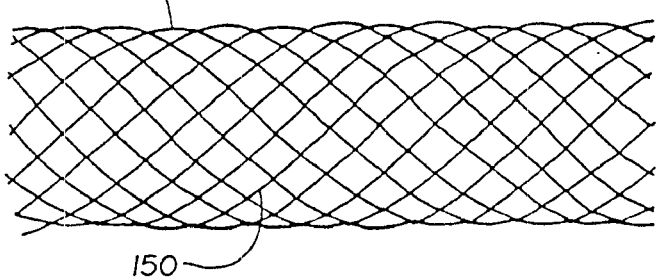
FIG. 14 is a schematic showing of a braided stent made up of a plurality of strands.
Figure 15:
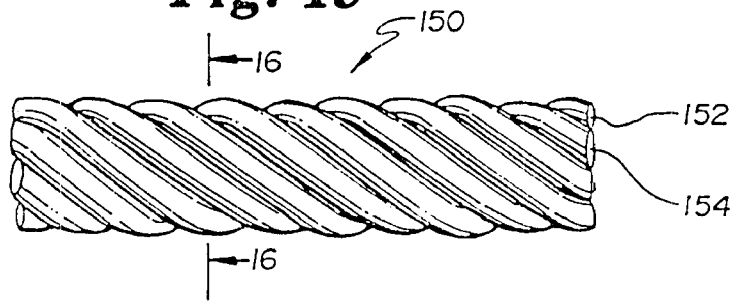
FIG. 15 is a detail of a single strand from the stent of FIG. 14 showing that the strand is made up of a plurality of wires of two different types.
Figure 16:
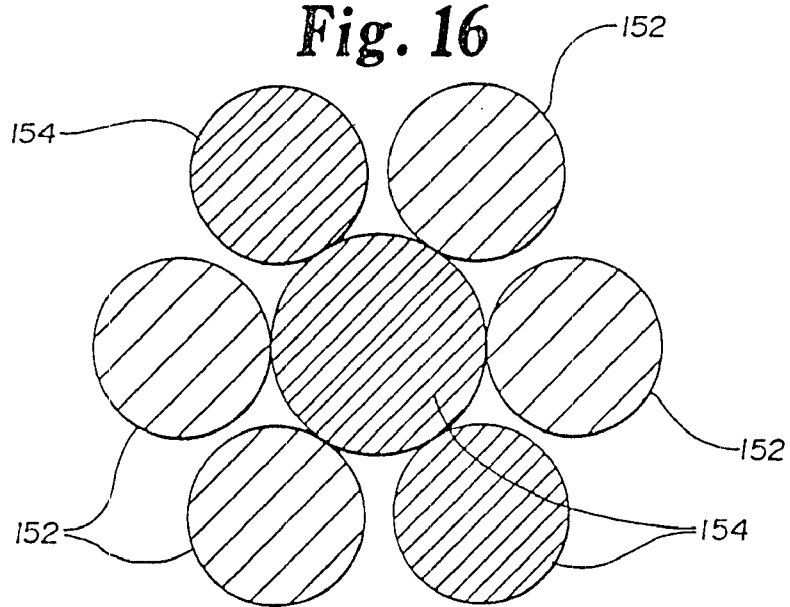
FIG. 16 is a cross-sectional view taken along line 16—16 of FIG. 15 showing the two different types of wire.

Referring now to FIGS. 14–16, a multi-strand braided stent is shown in FIG. 15. Each strand 150 in the stent is a micro-cable. That is, each strand is made up of a plurality of wires 152 and 154 as is seen in FIGS. 15 and 16. Each of the wires 152 and 154 consists of two different nitinol alloys as seen best in FIG. 16, or one nitinol and one ordinary metal such as stainless steel, platinum or tantalum. The latter two would provide enhanced radiopacity. One nitinol alloy wire 154 has an austenitic finish ($A_f$) temperature less than body temperature. The other wire 152 could be nitinol having an $A_s$ (austenitic start) greater than body temperature. Also, it could be an ordinary metal. Additionally, one or more of the strands may be of a biodegradable material such as a plastic or may be of a material including an absorbable drug.

Since the two alloys are stranded into micro-cable one does not have to engage in selective, discrete heat treating methods to produce both shape memory and martensitic effects.

Radiopaque portions or coatings may be included on any parts of these stents as is known in the prior art.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A tissue supporting device comprising a constrainable, self-expanding member of generally tubular shape, said member comprising a first layer of a resilient self-expandable material and a second layer of a deformable and substantially less resilient material than the first layer, said second layer being deformable by an external force but being non-self-expandable; the member being constrainable to a deployable diameter in preparation for insertion into a patient; the member being self-expanding when unconstrained to an initially deployed diameter due to the transformation of the first layer from a martensitic to an austenitic state; the first and second layers being affixed to each other or braided; the first and second layers being so associated with respect to each other such that the device may be further expanded due to the deformability of the second layer by an external force to radially enlarge the member to an enlarged self sustained fully deployed diameter for providing tissue support.

2. The device of claim 1 wherein the first and second portions are of metal.

3. A tissue supporting device comprising a constrainable, self-expanding member of generally tubular shape, said member comprising a first layer of a resilient self-expandable material and a second layer of a deformable and substantially less resilient material than the first layer, said second layer being deformable by an external force but being non-self-expandable; said first and second layers being discrete portions in the circumference of said tissue supporting device; the member being constrainable to a deployable diameter in preparation for insertion into a patient; the member being self-expanding when unconstrained to an initially deployed diameter due to the transformation of the first layer from a martensitic to an austenitic state; the first and second layers being so associated with respect to each other such that the device may be further expanded due to the deformability of the second layer by an external force to radially enlarge the member to an enlarged fully deployed diameter for providing tissue support.

4. A tissue supporting device comprising a constrainable, self-expanding member of generally tubular shape, said member comprising a first layer of a resilient self-expandable material and a second layer of a deformable and substantially less resilient material than the first layer, said second layer being deformable by an external force but being non-self-expandable; said first and second layers being comprised of a shape memory alloy; the member being constrainable to a deployable diameter in preparation for insertion into a patient; the member being self-expanding when unconstrained to an initially deployed diameter due to the transformation of the first layer from a martensitic to an austenitic state; the first and second layers being so associated with respect to each other such that the device may be further expanded due to the deformability of the second layer by an external force to radially enlarge the member to an enlarged fully deployed diameter for providing tissue support.

5. A tissue supporting device comprising a constrainable, self-expanding member of generally tubular shape, said member comprising a first layer of a resilient self-expandable material and a second layer of a deformable and substantially less resilient material than the first layer, wherein the first and second layers are of shape memory alloy, austenite and martensite, respectively, said second layer being deformable by an external force but being non-self-expandable; the member being constrainable to a deployable diameter in preparation for insertion into a patient; the member being self-expanding when unconstrained to an initially deployed diameter due to the transformation of the first layer from a martensitic to an austenitic state; the first and second layers being affixed to each other or braided; the first and second layers being so associated with respect to each other such that the device may be further expanded due to the deformability of the second layer by an external force to radially enlarge the member to an enlarged self sustained fully deployed diameter for providing tissue support.

6. The device of claim 1 wherein the first and second portions are of a shape memory alloy.

7. A tissue supporting device comprising a constrainable, self-expanding member of generally tubular shape further comprising a predetermined fabricated diameter; said member comprising a first layer of resilient self-expandable material and a second layer of a deformable and substantially less resilient material than the first layer, said second layer being deformable by an external force but being non-self-expandable; the member being constrainable to a deployable diameter in preparation for insertion into a patient; the member being self-expanding when unconstrained to an initially deployed diameter due to the resiliency of the first layer; the first and second layers being so associated with respect to each other such that the device may be further expanded due to the deformability of the second layer by an external force to radially enlarge the member to an enlarged fully deployed diameter for providing tissue support; wherein at normal body temperatures the first layer is comprised of a shape-memory, superelastic austenite alloy layer and the second layer is comprised of a shape-memory, martensite alloy layer; the superelastic austenite alloy layer having a transition temperature from martensite to austenite less than body temperature while the martensite alloy layer has a transition temperature from martensite to austenite greater than body temperature, the martensite alloy layer and the superelastic austenite alloy layer being constructed, arranged and associated with respect to each other such that the two alloy layers act in combination to allow constraint of the stent to a deployment diameter smaller than the predetermined fabricated diameter, and upon transformation of the first layer from martensite back to austenite to self-expand the stent back to a self-expanded diameter that is about the predetermined fabricated diameter at temperatures in excess of the transition temperature of the first layer, the shape memory of the superelastic austenite first layer tending to form the stent to a larger diameter than the predetermined fabricated diameter and the self-expanded diameter due to its shape memory but being restrained therefrom by the second martensite alloy layer, wherein the first layer can be deformed by external force. along with the second layer to an enlarged stent diameter beyond that of the selfexpanded diameter.

8. The tissue supporting device of claim 7 wherein the first and second portions are in the form of layers in overlying relationship.

9. The tissue supporting device of claim 7 wherein the alloy composition is about 50Ni/50Ti atomic weight percent.

10. The tissue supporting device of claim 7 wherein the alloy composition is a cold worked alloy.

11. The tissue supporting device of claim 7 wherein the alloy composition is a prestrained alloy.

12. The tissue supporting device of claim 7 wherein the alloy composition exhibits cycle amnesia.

13. A permanent self-expanding stent for providing permanent tissue support, said stent having a generally tubular body of a predetermined fabricated diameter and being comprised, at about normal body temperatures, of a first layer comprised of a shape-memory, superelastic, austenite alloy and a second layer comprised of a shape memory, martensite alloy; the shape-memory, superelastic austenite alloy layer having a transition temperature from martensite to austenite less than body temperature while the martensite alloy layer has a transition temperature from martensite to austenite greater than body temperature, the martensite alloy layer and superelastic austenite alloy layer being constructed, arranged and associated with respect to each other such that the two alloy layers act in combination to allow constraint of the stent to a deployment diameter smaller than the predetermined fabricated diameter and upon transformation of the first layer from martensite back to austenite to self-expand the stent back to a self-expanded diameter that is about the predetermined fabricated diameter at temperatures in excess of the transition temperature of the first layer, the shape memory of the superelastic austenitic first layer tending to form the stent to a larger diameter than the self-expanded diameter and the predetermined fabricated diameter due to its shape memory but being restrained therefrom by the second martensitic alloy layer, wherein the first layer can be deformed by external force along with the second layer to an enlarged stent diameter beyond that of the self-expanded diameter.

14. A permanent self-expanding stent having a generally tubular body of a predetermined fabricated diameter comprised, at about normal body temperatures, of a shape-memory, superelastic, austenite alloy layer and a shape memory, martensite alloy layer, the superelastic austenite alloy layer having a transition temperature from martensite to austenite less than body temperature while the martensite alloy layer has a transition temperature from martensite to austenite greater than body temperature, the martensite alloy layer and superelastic austenite alloy layer being constructed, arranged and associated with respect to each other in comprising the stent such that the two alloy layers act in combination to allow, upon transformation of the austenite alloy layer to martensite at a temperature below the transition temperature, constraint of the stent to a deployment diameter smaller than the predetermined fabricated diameter and upon transformation of the austenite alloy layer from martensite back to austenite to self-expand the stent back to about the predetermined fabricated diameter at temperatures in excess of the transition temperature of the austenite superelastic layer, the shape memory of the superelastic austenite layer tending to form the stent to a larger diameter due to its shape memory but being restrained therefrom by the martensite alloy layer wherein the austenite alloy layer can be deformed by external force without plastic deformation along with the martensite layer to an enlarged stent diameter beyond that of the self-expanded diameter.

15. A permanent self-expanding stent having a generally tubular body of a predetermined fabricated diameter, comprised, at about normal body temperatures, of a shape-memory, superelastic, austenite phase layer and a shape memory, martensite phase layer, the superelastic austenite phase layer having a transition temperature from martensite to austenite less than body temperature while the martensite phase layer has a transition temperature from martensite to austenite greater than body temperature, the martensite phase layer and superelastic austenite phase layer being constructed, arranged and associated with respect to each other in comprising the stent such that the two layers act in combination to allow, upon transformation of the austenite phase layer to martensite, constraint of the stent to a deployment diameter smaller than the predetermined fabricated diameter and upon transformation of the austenite phase layer from martensite back to austenite to self-expand the stent back toward the predetermined fabricated diameter at temperatures in excess of the transition temperature of the austenite superelastic layer, the shape memory of the superelastic austenitic layer tending to form the stent to the fabricated diameter due to its shape memory but being restrained therefrom by the martensite layer wherein the austenite layer recovery back toward the fabricated diameter can be assisted by external force along with the deforming of the martensite layer without slip deformation to an enlarged stent diameter beyond that of the fabricated diameter.

16. The tissue supporting device of claim 1 wherein the first and second portions are mechanically joined, welded together, bonded together or joined by vapor deposition or ion beam deposition of the first portion onto the second portion.

* * * * *